United States Patent [19]

Hardee

[11] Patent Number: 6,039,751
[45] Date of Patent: Mar. 21, 2000

[54] SUPPORT DEVICE FOR NEWLY CROPPED EARS OF DOGS

[76] Inventor: Cynthia G. Hardee, 117 Arlington Ave., Colonial Heights, Va. 23834

[21] Appl. No.: 09/263,537

[22] Filed: Mar. 8, 1999

[51] Int. Cl.[7] ....................................................... A61F 5/08
[52] U.S. Cl. ........................................... 606/204.15; 602/6
[58] Field of Search ....................... 606/204.15, 204.25, 606/204.35, 204.45, 204.55; 602/46, 53, 6; 128/888, 893; 2/454

[56] References Cited

U.S. PATENT DOCUMENTS

| | | | |
|---|---|---|---|
| 2,600,025 | 6/1952 | Sage | 606/204.15 |
| 3,257,909 | 6/1966 | Robertson et al. | 119/96 |
| 3,881,472 | 5/1975 | Lee | 602/6 |
| 3,970,080 | 7/1976 | White | 128/82 |
| 4,275,715 | 6/1981 | Wolfe | 128/76 R |
| 4,872,219 | 10/1989 | Duncan | 128/866 |

*Primary Examiner*—Michael Buiz
*Assistant Examiner*—Kevin Truong
*Attorney, Agent, or Firm*—Norman B. Rainer

[57] ABSTRACT

A device for supporting newly cropped ears of dogs includes an outer member elongated upon a straight axis and fabricated as a monolithic piece of closed cell polymer foam material bounded by concave interior and convex exterior cylindric surfaces. A protective piece of thin plastic material is adhered to the interior surface in a manner to preserve its concave contour. The upper and lower extremities of the device are easily trimmable so as to cause the device to conform to ears of different size and varied upper tip contour.

8 Claims, 1 Drawing Sheet

6,039,751

SUPPORT DEVICE FOR NEWLY CROPPED EARS OF DOGS

BACKGROUND OF THE INVENTION

1. Field of the Invention

This invention relates to the treatment of animals' ears such as after cosmetic surgery to trim the ears, or such as during the period that the ears are healing following traumatic injuries. More particularly, it relates to supporting an ear in need of healing by attaching a soft, pliable, self-supporting body that conforms substantially to the interior surface of the ear against such interior surface to yieldably hold the ear in a generally erect condition until the ear has sufficiently healed to support itself.

2. Description of the Prior Art

While the general concept of holding the ears of a dog or other animal in an erect condition following cosmetic surgery to trim the ears for appearance purposes or for holding them in such condition after traumatic injury is not new per se, prior devices have included awkward structures in the nature of wire frames placed on the animal's head and attached to the outside of the ears. Such structures, as disclosed for example in U.S. Pat. Nos. 3,257,990 and 4,275,715, are highly undesirable for a number of reasons, not the least of which is the fact that such frames are difficult to keep in place and may cause serious injury when the animal shakes his head violently or rubs it against other objects in an effort to be rid of the irritating adornment.

U.S. Pat. No. 3,970,080 discloses an ear supporting device fabricated by molding a soft plastic material within the dog's ear so that the resultant device retains the exact impression of the interior of the dog's ear. Such fabrication technique is a difficult experience for the dog which must be sedated, and the resultant product is expensive and customized for a single specific dog.

Therefore, it is one important object of the present invention to provide an animal ear support having a body that fits neatly into and lies against the interior surface of the animal's ear so as to hold the ear in a generally erect condition, without the use of exterior metal frames and the like, until damaged or surgically weakened cartilage in the ear can regain its normal strength and rigidity to support the ear on its own.

Another important object of this invention is to provide a support as above-described wherein its body is stiff enough to provide the required degree of support for the healing ear and yet is sufficiently soft and pliable to flex with the ear under certain conditions so as to remain in place and prevent bruising of the ear should it be brushed against solid objects.

Another important object of this invention is the provision of a support as aforesaid which may be readily provided in a number of assorted sizes to accommodate various breeds of dogs, for example, and which is sufficiently inexpensive to fabricate that it can be disposed of after each use.

An additional important object is to provide an ear support which is readily adapted to be trimmed in certain areas as may be required to properly fit the animal's ear without extending outwardly beyond its edges.

A still further important object of the present invention is the provision of supporting body that can be readily attached and detached from an animal's ear.

These objects and other objects and advantages of the invention will be apparent from the following description.

SUMMARY OF THE INVENTION

The above and other beneficial objects and advantages are accomplished in accordance with the present invention by a disposable ear support device comprising:

a) an outer member elongated upon a straight axis and fabricated as a monolithic piece of closed cell polymer foam material bounded by upper and lower transverse edges, parallel concave interior and convex exterior cylindric surfaces having uniform curvatures centered upon said axis, and opposed longitudinal edges, and b) a protective piece of thin plastic material adhered to the interior surface of said outer member in a manner to preserve the concave contour of said interior surface, and extending from said upper transverse edge part way toward said lower transverse edge.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
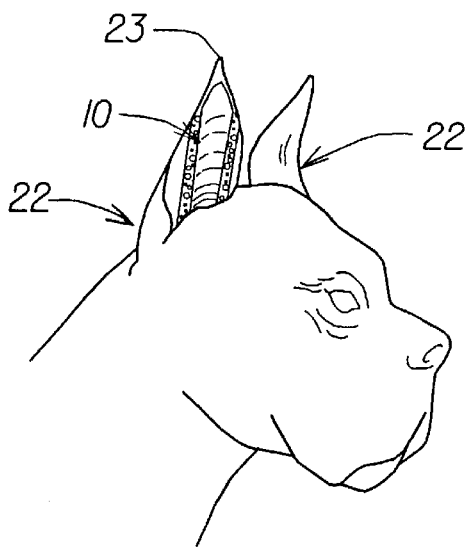
FIG. 1 is a perspective view of a dog's head showing the device of the present invention attached to the ears of the dog.
Figure 2:
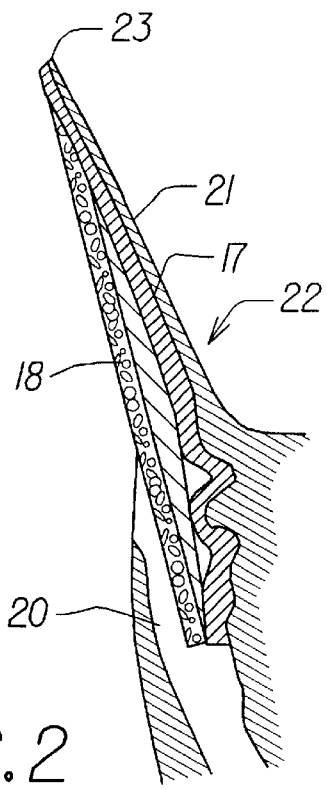
FIG. 2 is an enlarged, fragmentary vertical cross-sectional view through the head showing the manner in which the device supports the ear.
Figures 3, 5:
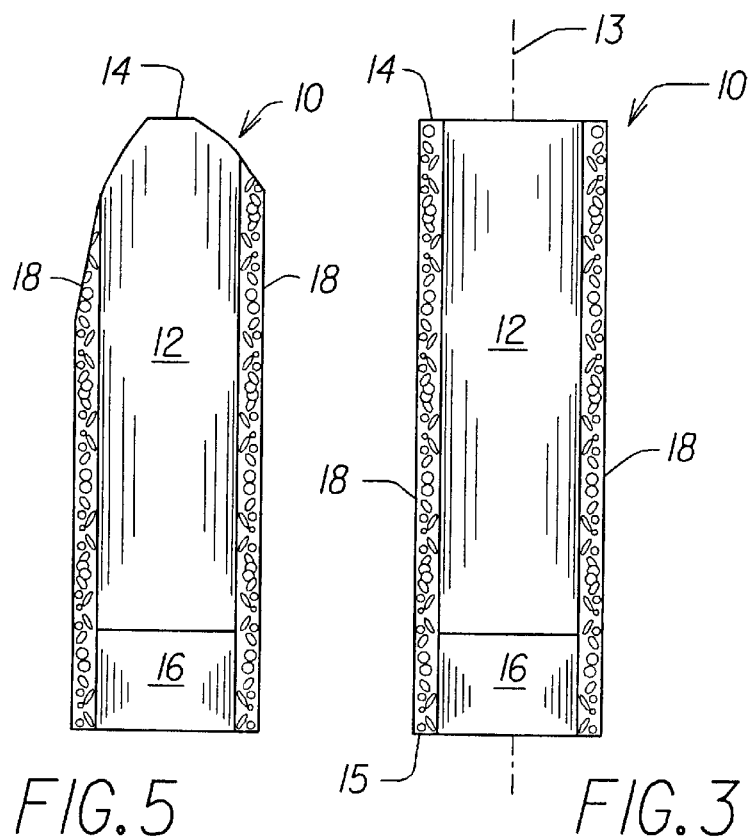
FIG. 3 is a front view of an embodiment of the device of the present invention.
FIG. 5 is a view such as FIG. 3, following the cutting away of portions to conform to the ear of a particular dog.
Figure 4:
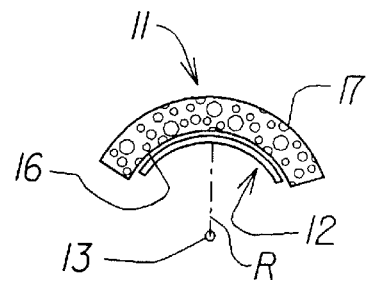
FIG. 4 is a top view of the embodiment of FIG. 3.

Referring to FIGS. 1–5, an embodiment of the ear support device 10 of the present invention is shown comprised of outer member 1 and attached protective piece 12.

Outer member 11 is elongated upon a straight axis 13, and is bounded by upper and lower transverse edges 14 and 15, respectively, concave interior and convex exterior parallel cylindric surfaces 16 and 17, respectively, having uniform curvature centered upon axis 13, and opposed longitudinal edges 18. Said outer member 11 is preferably fabricated of a monolithic piece of closed cell polymer foam such as polyethylene, polyurethane, neoprene or rubber. The foam, whether by virtue of polymer selection or physical factors is a self-supporting, yet resilient material. The closed cell nature of the foam causes it to be more sanitary because it will prevent entrance of water, microbial contaminants, and insects. The expression "cylindric" is intended to denote a fragmentary surface which, if viewed in its entirety, would be a cylindrical surface, namely a surface generated by a straight line moved in a circuitous path around and parallel to a stationary line. When said path is circular, said surface is considered to be a circular cylindrical surface. The preferred configuration of the aforesaid interior and exterior surfaces is in fact a portion, comprised of between about 70 and 120 degrees of arc of a circular cylindrical surface.

The thickness of outer member 11, namely the distance measured orthogonally between said interior and exterior surfaces, may range between 6 and 12 millimeters. The length of said outer member, measured axially between said upper and lower edges, may range between 4 and 8 inches. The radius of curvature of said interior surface, denoted by the symbol R in FIG. 4, may range between 0.75 and 1.25 inch. Suitable materials for use in fabricating outer member 11 may be found in commerce as thermal insulating material for pipes.

Protective piece 12 is a thin monolithic sheet of plastic material adhered to interior surface 16 of said outer member in a manner to conform with the concave contour of said surface. Said protective piece is positioned in a manner extending part way from upper transverse edge 14, said "part way" being preferably between 60% and 85% of the overall length of said outer member. Protective piece 12 is of a resilient nature. Its purpose is to protect outer member 11 from the dog's scratching efforts to dislodge the device.

The device of this invention is employed after the dog's cropped ears have healed, and the stitches have been removed. In use, the lower portion of the device is trimmed, as with shears or a razor blade, to fit the dog's ear canal 20. The upper portion of the device is similarly trimmed to conform with the upper portions of pinna 21 and tip 23 of ear 22.

The hair within the dog's ear is then preferably removed by cutting or shaving. A skin bonding composition is then applied to exterior surface 17. Suitable compositions are those available under the names "Smith and Nephew," "Vi-Drape" sold by Parke, Davis and Company, and "Silastic Medical Adhesive" sold by Dow Corning Corporation. The adhesive may also be applied to the dog's inner ear base, pinna and tip. The device is then inserted into the ear, and pressed against the several portions of the ear to secure good contact. The drying time for securing bonding should be 4 to 5 minutes. The installed support device is expected to last 2 to 3 weeks. The device can be removed by peeling away slowly, beginning at the tip of the ear. The removed device is discarded.

It will be appreciated from the foregoing that the ear support 10 of the present invention provides a significant improvement over the known prior ear supports, such as, for example, the headmounted frame-type supports which attach to the outside surfaces of the animals' ears. The soft, pliable nature of the support device is non-irritating to the animal, in contrast to such rigid frames, and its softness and pliability help to not only maintain adhesion to the ear but also help to preclude any injury to the ear. In these regards, if the device were rigid and unyielding, it is quite likely that it would be unable to withstand the centrifugal forces which are generated when an animal shakes his head violently. Moreover, if the device were unyielding, such characteristic could quite possibly lead to serious bruising or mutilating of the ear should the dog brush up against solid objects or paw aggressively at his ear.

The support 10 can, of course, be of considerable assistance in a number of different situations. One example of such usage is where the dog's ears have been trimmed for cosmetic purposes. Following such minor surgery, it is necessary to maintain the ears in a substantially erect condition until such time as the cartilage has strengthened sufficiently that it can hold the ears in an erect condition without assistance of some artificial support. Another situation arises were the dog may have been involved in altercations with another dog, resulting in ear damage. It may be necessary in that situation to support the ear firmly while the ear tissue and cartilage heal and medication is applied. Moreover, in such situations of traumatic injury to the ear, it may be necessary for the veterinarian to perform surgery, in which event, cartilage may be weakened, requiring fairly prolonged support from an external source.

It should also be apparent that the relatively non-complex nature of the ear support 10 of the present invention allows the same to be produced rather economically such that it may be considered a disposable item. Because the lowermost portion of the device does not occupy the entire cross-sectional area of ear canal 20, the canal can receive sufficient fresh air to keep that area of the ear well aerated. This serves to minimize the advent of infections that are augmented by moist conditions.

While particular examples of the present invention have been shown and described, it is apparent that changes and modifications may be made therein without departing from the invention in its broadest aspects. The aim of the appended claims, therefore is to cover all such changes and modifications as fall within the true spirit and scope of the invention.

Having thus described my invention, what is claimed is:

1. A disposable device for supporting dog's ears, said device comprising:

a) an outer member elongated upon a straight axis and fabricated as a monolithic piece of closed cell polymer foam material bounded by upper and lower transverse edges, parallel concave interior and convex exterior cylindric surfaces having uniform curvatures centered upon-said axis, and opposed longitudinal edges, and b) a protective piece of thin plastic material adhered to the interior surface of said outer member in a manner to preserve the concave contour of said interior surface, and extending from said upper transverse edge toward said lower transverse edge.

2. The device of claim 1 wherein said outer member is resilient and self-supporting.

3. The device of claim 2 wherein said cylindric surfaces are circular cylindric surfaces.

4. The device of claim 3 wherein said cylindric surfaces are comprised of between 70 and 120 degrees of arc of a circular cylindric surface, as measured between said longitudinal edges.

5. The device of claim 4 wherein the distance measured orthogonally between said interior and exterior surfaces is between 6 and 12 millimeters.

6. The device of claim 5 wherein the length of said outer member, measured axially between said upper and lower edges is between 4 and 8 inches.

7. The device of claim 6 wherein the radius of curvature of said interior surface is between 0.75 and 1.25 inch.

8. The device of claim 7 wherein said exterior surface is adherable to a conventional skin bonding composition.

* * * * *